United States Patent [19]
McCombs

[11] Patent Number: 5,871,564
[45] Date of Patent: Feb. 16, 1999

[54] PRESSURE SWING ADSORPTION APPARATUS

[76] Inventor: Norman Richard McCombs, 109 Millwood Dr., Tonawanda, N.Y. 14150

[21] Appl. No.: 876,749

[22] Filed: Jun. 16, 1997

[51] Int. Cl.[6] .................................................. B01D 53/053
[52] U.S. Cl. ..................................... 95/98; 95/100; 95/105; 95/119; 95/122; 95/130; 96/116; 96/130; 96/133; 96/144
[58] Field of Search ............................... 95/98, 100–105, 95/119, 122, 130; 96/115, 116, 130, 133, 144

[56] References Cited

U.S. PATENT DOCUMENTS

| | | | |
|---|---|---|---|
| D. 311,061 | 10/1990 | Vrana et al. | D24/8 |
| 4,065,272 | 12/1977 | Armond | 95/130 X |
| 4,100,421 | 7/1978 | Tabata et al. | 96/115 X |
| 4,194,890 | 3/1980 | McCombs et al. | 96/130 X |
| 4,263,018 | 4/1981 | McCombs et al. | 96/130 X |
| 4,440,548 | 4/1984 | Hill | 96/115 X |
| 4,472,177 | 9/1984 | Sircar | 96/130 X |
| 4,545,790 | 10/1985 | Miller et al. | 96/130 X |
| 4,802,899 | 2/1989 | Vrana et al. | 55/161 |
| 4,892,566 | 1/1990 | Bansal et al. | 55/26 |
| 4,917,710 | 4/1990 | Haruna et al. | 95/102 |
| 4,927,434 | 5/1990 | Cordes et al. | 96/115 X |
| 4,973,339 | 11/1990 | Bansal | 55/31 |
| 5,101,820 | 4/1992 | Christopher | 128/204.18 |
| 5,122,164 | 6/1992 | Hirooka et al. | 95/98 X |
| 5,250,088 | 10/1993 | Yamaguchi et al. | 95/98 |
| 5,340,381 | 8/1994 | Vorih | 95/130 X |
| 5,407,465 | 4/1995 | Schaub et al. | 95/102 X |
| 5,419,314 | 5/1995 | Christopher | 128/200.26 |
| 5,474,595 | 12/1995 | McCombs | 95/23 |
| 5,490,871 | 2/1996 | Coates et al. | 95/105 X |
| 5,531,807 | 7/1996 | McCombs | 95/26 |
| 5,593,478 | 1/1997 | Hill et al. | 96/115 X |
| 5,711,787 | 1/1998 | Neill et al. | 95/130 X |

*Primary Examiner*—Robert Spitzer
*Attorney, Agent, or Firm*—Jaeckle Fleischmann & Mugel, LLP

[57] ABSTRACT

A pressure swing adsorption apparatus to vary selectively the concentration of at least one constituent of a gaseous mixture by sending a gaseous mixture into an adsorber to generate a particular product gas while delivering to another adsorber both a predetermined portion of the product gas to purge the other adsorber of its adsorbed gas and a selected amount of the product gas, independent of the flow rate and in addition to the predetermined portion, to produce a desired relative concentration of the constituents of the product gas from a range of relative concentrations.

29 Claims, 9 Drawing Sheets

PRESSURE SWING ADSORPTION APPARATUS

FIELD OF THE INVENTION

This invention relates generally to a gas concentrator apparatus for separating gas mixtures by pressure swing adsorption and relates more particularly to the production of a product gas having a desired concentration and flow rate of a particular gas.

BACKGROUND OF THE INVENTION

The general type of pressure swing adsorption apparatus with which this invention is concerned is set forth in U.S. Pat. Nos. 4,802,899 and 5,531,807. Generically, a pressure swing adsorption apparatus includes a pair of adsorbers each having a fixed bed of adsorbent material disposed between an inlet and an outlet for accommodating a flow of gas therethrough. The adsorbent material of each adsorber fractionates at least one constituent gas from a gaseous mixture when the gaseous mixture from a feed stream is sequentially directed through the inlet and the outlet of one adsorber. That direction is called a co-current direction. While one adsorber performs adsorption the other adsorber is simultaneously purged of adsorbed constituent with product gas that is withdrawn from the outlet of one adsorber and directed through the outlet of the other adsorber to the inlet of the other adsorber. That direction is called a counter-current direction. Once the other adsorber is purged, the gaseous mixture is directed into the inlet of the other adsorber so that the other adsorber performs adsorption while the one adsorber is simultaneously purged of adsorbed constituent with product gas withdrawn from the outlet of the other adsorber.

Figure 1A:
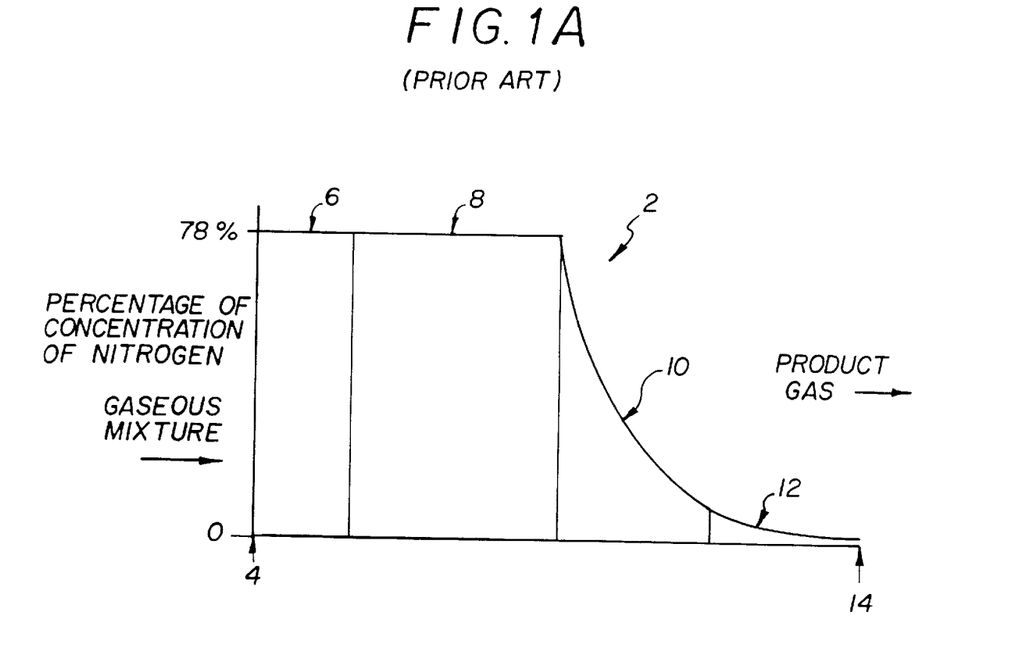
FIG. 1A is a graph of the concentration of $N_2$ in air as it proceeds through an adsorber designed to generate a high concentrated product gas. (Prior Art)

Highly concentrated product gas is attained by controlling the zones of the adsorber. A conventional-adsorber contains four zones as illustrated in FIG. 1A. When compressed air enters the adsorber 2 through the input 4, the air contains about 78% nitrogen, 21% oxygen, 0.9% argon, and a variable amount of water. The first zone or water zone 6, captures the water. The second zone 8 adsorbs the fractionated nitrogen and a lesser degree oxygen. The third zone or mass transfer zone ("MTZ") 10 comprises a varied concentration of product oxygen gas that increases in concentration in relation to the distance from the second zone 8 by capturing more fractionated nitrogen. The fourth zone 12 comprises the high concentrated product oxygen gas and extends to the terminal end 14 of the adsorber 2. Controlling a pressure swing adsorption apparatus to attain a product gas having a relatively high concentration of a particular gas, like oxygen, is conventional.

The high concentrated product oxygen gas is achieved by stabilizing the water zone 6 near the input 4 of the adsorber 2 and maintaining the MTZ 10 as a sharp demarcation between the second and fourth zones 8, 12. These zones 6, 10 are stabilized and maintained by directing certain quantities of product oxygen gas counter-currently through the adsorber 2.

Some applications, however, require a lower concentration of product oxygen gas. Controlling the apparatus to produce a product oxygen gas having a desired and specific concentration and flow rate in which these characteristics are independent of each other is an object of this present invention.

In the past, there have been proposals to attain the desired concentration of product oxygen gas in a pressure swing adsorption apparatus. One such proposal entails blending the gaseous air mixture from the feed stream with the high concentrated product oxygen gas. Such a proposal has numerous adverse effects on the product oxygen gas. One such adverse affect is that the concentration of product oxygen gas is dependent upon the flow of the gaseous mixture. Thus, when the flow of gaseous mixture is disturbed the concentration of product gas is also affected. Another adverse effect is that the gaseous mixture is compressed and therefore potentially "wet." This "wet" gaseous mixture when blended with product gas can cause condensation in the product oxygen gas which may not be desired.

Figure 1B:
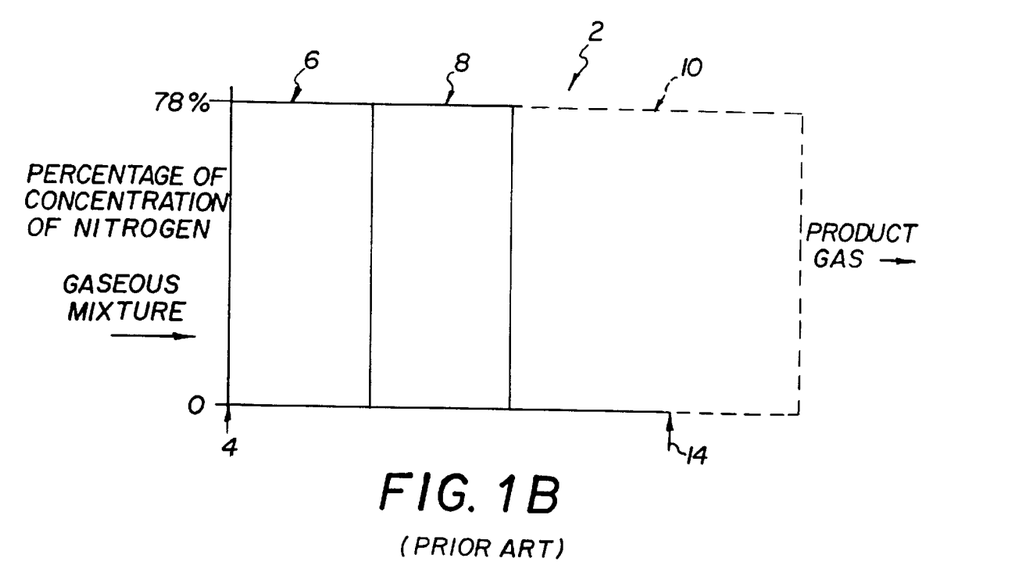
FIG. 1B is a graph of the concentration of $N_2$ in air as it proceeds through an adsorber designed to generate a lower concentrated product gas. (Prior Art)
Figure 1C:
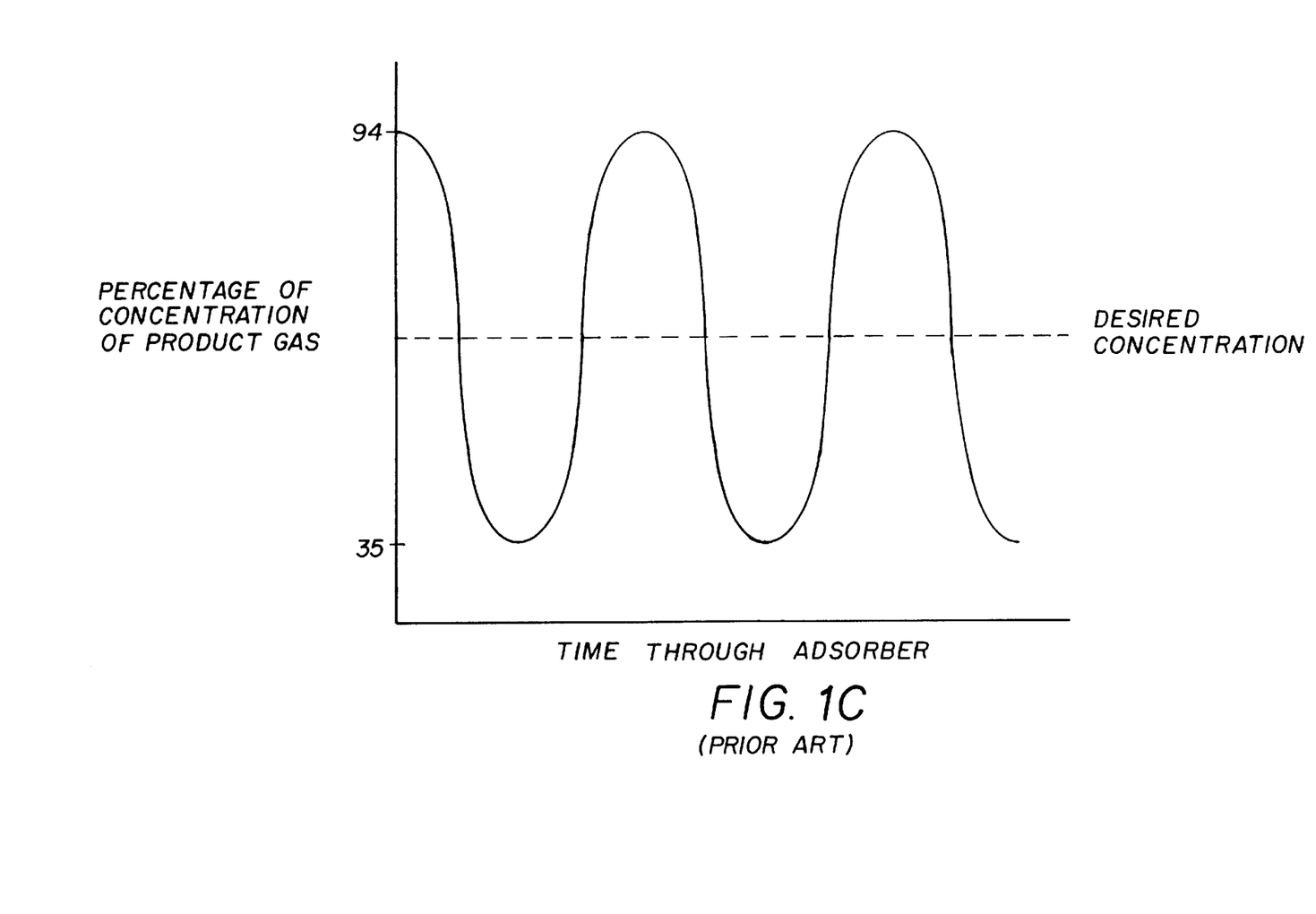
FIG. 1C is a graph of the concentration range of product gas produced from an adsorber illustrated in FIG. 1B. (Prior Art)

Another proposal would overdraw the pressure swing adsorption apparatus. Overdrawing occurs when the product oxygen gas is drawn from adsorber 2 at a high flow rate. The high flow rate moves and extends first zone 6, second zone 8, and MTZ 10. In particular, the MTZ 10 moves and extends through and beyond the terminal end 14 of the adsorber 2 as illustrated in FIG. 1B. When the MTZ 10 reaches and extends through the terminal end 14 the product oxygen gas is withdrawn at an unknown and uncontrollable lower concentration. Overdrawing has a number of disadvantages. First, the efficiency of the apparatus is compromised because it is difficult to stabilize the water zone 6 when the MTZ 10 moves and extends through to the terminal end 14. Second, it is difficult to control the MTZ 10 when the MTZ 10 is at the terminal end 14, which in turn makes it difficult to control the concentration range of the product oxygen gas generated from the adsorber 2 as illustrated in FIG. 1C. Third, it is difficult to duplicate for a particular concentration. Lastly, the flow rate and the concentration of the product gas are intrinsically dependent upon each other since the flow rate controls the concentration level of product gas.

In yet another proposal disclosed in U.S. Pat. No. 5,531,807, a pressure swing adsorption apparatus comprises a flow controller that regulates the flow rate of the product gas. It was proposed that if the flow controller discharges the high concentrated product gas at about 7 liters per minute, the product gas would decrease in concentration. This proposal, however, did not disclose how to control the concentration level of the product gas.

It is an object of the present invention to provide a new and improved pressure swing adsorption apparatus (oxygen concentrator) wherein the apparatus can be set to attain variously desired concentrations and flow rate of product oxygen gas wherein the flow rate and concentration are independent of each other.

SUMMARY OF THE INVENTION

A pressure swing adsorption apparatus fractionates at least one constituent from a gaseous mixture by sending a gaseous mixture into a first adsorber to generate a particular product gas. The apparatus has a valve in a second purge loop that independently controls the adsorber to produce a desired concentration of the product gas from a range of available concentrations. Once the desired concentration of the product gas is independently attained, the apparatus is capable of independently controlling the flow rate of the product gas from the concentration of the product gas.

The foregoing and other objects, features and advantages of the invention, as well as presently preferred embodiments thereof and the best known techniques for fabricating product gas concentrators in accordance with this invention will become more apparent from a reading of the following description in connection with the accompanying drawing.

DETAILED DESCRIPTION OF THE ILLUSTRATED EMBODIMENT

Figure 3:
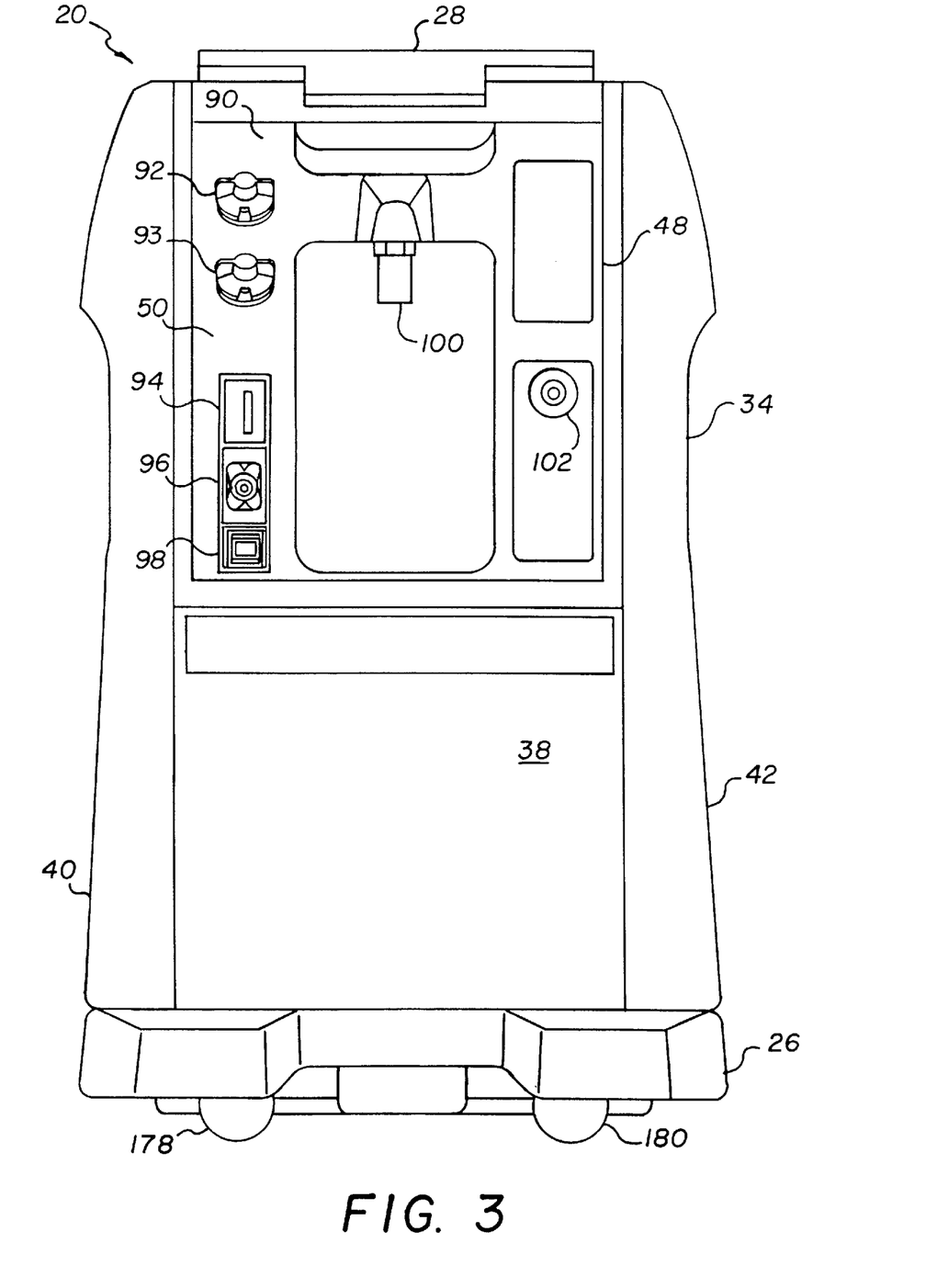
FIG. 3 is a front view of an oxygen concentrator in accordance with the present invention.

Turning now to the drawing and considering first FIG. 3, there is shown an embodiment, generally indicated 20, of a pressure swing adsorption apparatus in accordance with the present invention for fractionating at least one component or constituent from a gaseous mixture by pressure swing adsorption. Other embodiments regarding pressure swing apparatuses are hereby incorporated by reference in commonly assigned U.S. Pat. Nos. 4,802,899 and 5,531,807, the entire disclosures of which are incorporated by reference herein.

Figure 2:
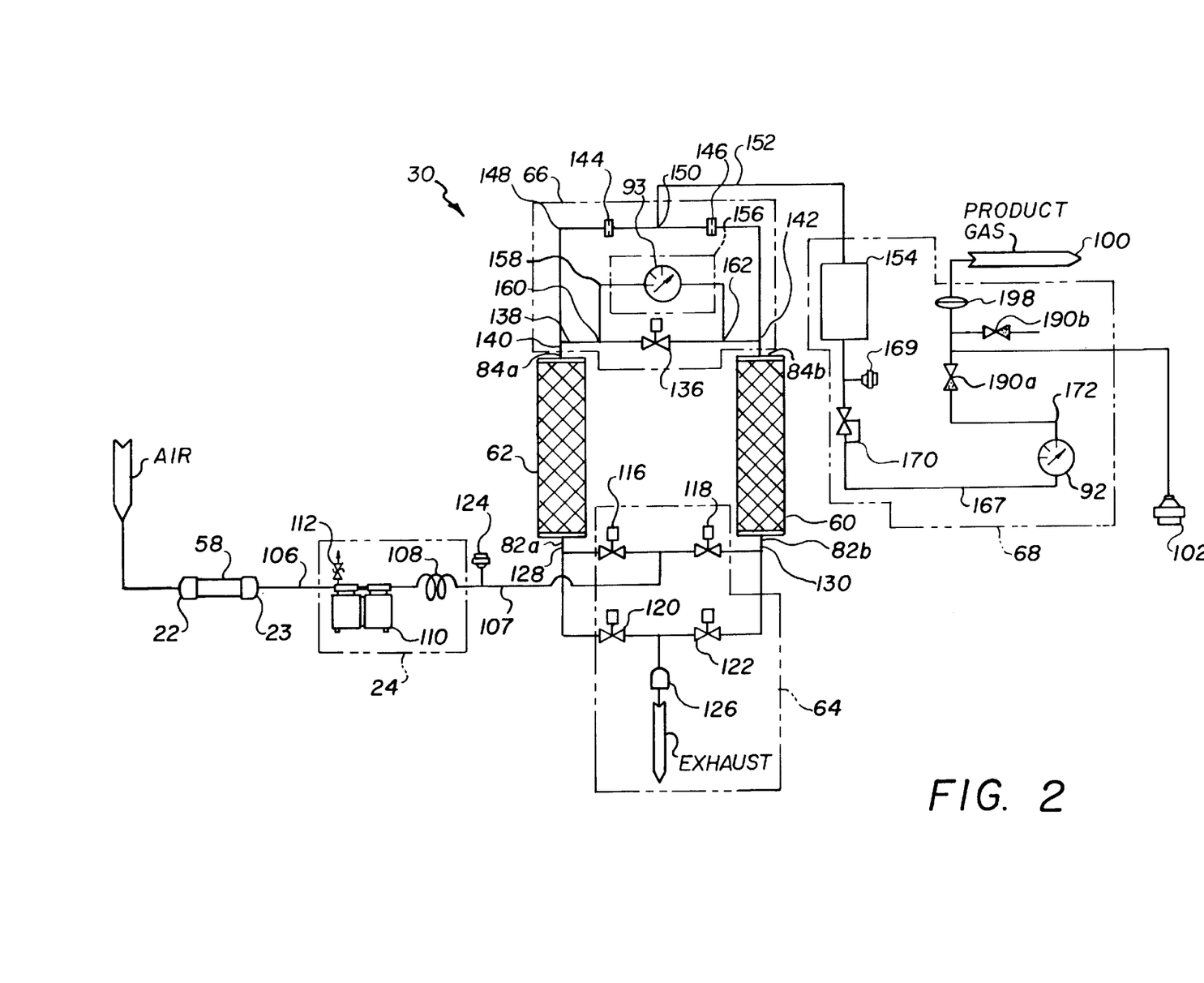
FIG. 2 is a schematic diagram illustrating the flow connections between working components of the oxygen concentrator.

With reference to FIG. 2, the gaseous air mixture is supplied to the apparatus 20 through an assembly of working components 30. The components 30 initially receive a feed gas stream in an input 22 of an intake resonator 58 to decrease the noise for the intake of the feed stream. The feed stream continues through resonator outlet 23 and is moved therealong through piping 106 by means of a pump or compressor assembly 24. Compressor assembly 24 containing compressor 110 and heat exchanger 108 moves the feed stream through assembly piping 107 to a valve block 64, in particular a first feed valve 116.

From feed valve 116 and through piping 128, the feed stream enters an inlet 82a of a first adsorber 62 in a co-current direction. While in adsorber 62 the feed stream fractionates into the desired concentration of product gas. The product gas then proceeds through outlet 84a of first adsorber 62 into the product manifold assembly 66.

Figure 6:
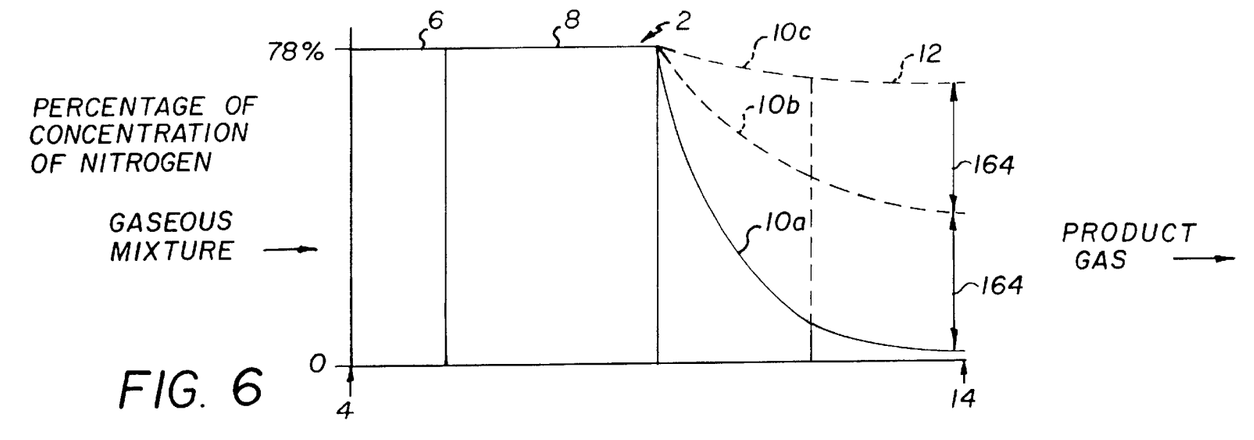
FIG. 6 is a graph of the concentration of $N_2$ in air as it proceeds through an adsorber designed to generate different desired concentrations of product gas.
Figure 7:
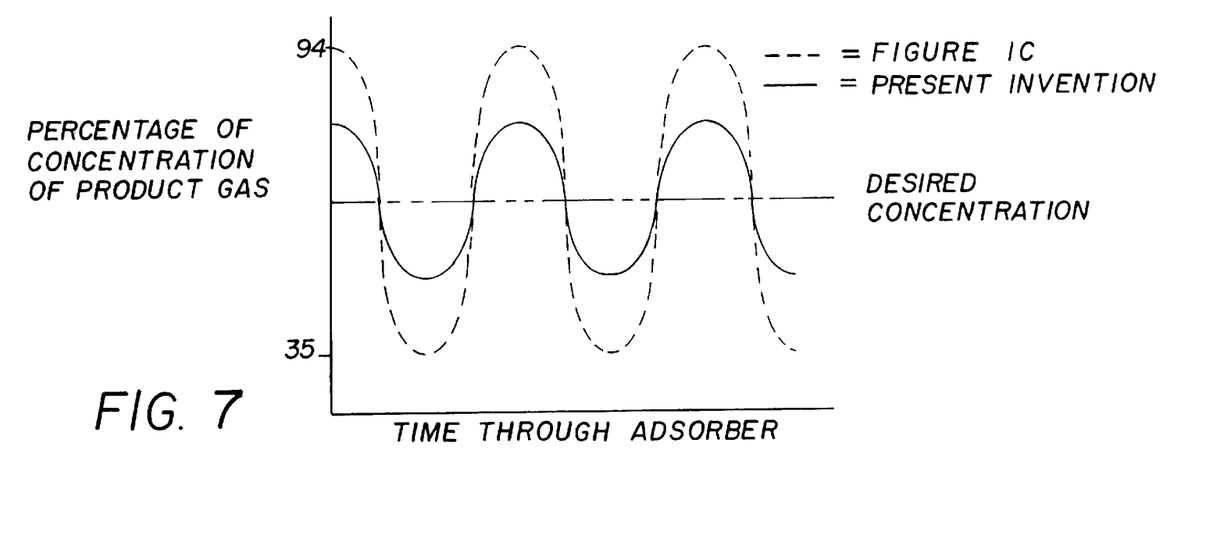
FIG. 7 is a graph of the resulting product gas concentration range produced from an adsorber illustrated in FIG. 9 in relation to the graph illustrated in FIG. 1C.

While in the product manifold 66 the product gas is controllably directed in three directions. The first direction is through T-connection 140 and piping 138 to product equalization valve 136. The second direction is through T-connection 140 and piping 148 to purge orifice 144. The last direction is through T-connections 140 and 160 and piping 138 and 158 to second purge loop 156, in particular a conventional concentration valve 93. If purge orifice 144 is open and concentration valve 93 is closed the concentration of the product gas will be high as shown in FIG. 1A. In the present invention purge orifice 144 and concentration valve 93 are open and together independently control the concentration of the product gas. In particular, orifice 144 and valve 93 control the position of MTZ 10 (possible positions include lines 10a, 10b and 10c and variations in-between as illustrated by arrow 164) and water zone 6 of second adsorber 60, as shown in FIG. 6, and the concentration range of the product gas, as shown in FIG. 7.

Returning to FIG. 2, a small portion of the product gas proceeds through purge orifices 144, 146, and T-connections 150, 142, and the product gas proceeding through valve 93 and T-connections 162, 142 are counter-currently directed through an outlet 84b and an inlet 82b of second adsorber 60. The counter-current product gas purges adsorber 60 and with the purged nitrogen then proceeds through piping 130 to valve block 64, in particular waste valve 122 and waste silencer 126 and then exhausted as shown. The other or usable portion of the product gas proceeding through purge orifice 144 is directed through T-connection 150 to flow control assembly 68.

Within the flow control assembly 68 are a mixing tank 154, a test block component 169, a pressure regulator 170, a conventional flow controller valve 92, check valves 190a, b, a conventional bacteria filter 198 and outlet connector 100. Mixing tank 154 receives the product gas through piping 152 and T-connection 150 to average the product gas to the desired concentration. Once through mixing tank 154 the product gas is pushed through piping 167 and monitored by pressure regulator 170 until it reaches the flow controller valve 92. The product gas flow rate is 20 independently controlled by the flow controller valve 92 to proceed through piping 172 and check valves 190a to outlet connector 100.

When adsorber 62 is saturated and adsorber 60 purged the above-process is reversed and adsorber 60 is used to produce oxygen concentrated product gas. The reverse process is the same as the above-process except for three differences. The first difference is that the feed stream from pump 24 is directed to feed valve 118 for adsorber 60. The second difference is that purge orifice 144 is reduced by purge orifice 146. The last difference is that waste valve 122 is replaced by waste valve 120. Thus a portion of product gas flows from adsorber 60 through purge orifice 146 to assembly 68 and the balance flows in a counter-current direction through valve 136 and second loop 156 to purge adsorber 62 and then exhausted along with purged nitrogen through valve 120 and silencer 126. The feed valves 116, 118 and waste valves 120, 122 are solenoid valve pairs. In each pair, one is open and the other is closed depending upon the direction of the gas through the respective adsorber 60, 62.

As will be apparent hereinafter, the apparatus 20 and components 30 are specifically described and illustrated in relation to the application of pressure swing adsorption to the fractionation of air to produce an oxygen-rich stream. Hence, the feed stream supplied to the apparatus 20 is compressed atmospheric air. Although the present description is limited to the production of desired concentration of oxygen product gas, it is apparent that skilled practitioners could use this pressure swing adsorption apparatus to produce other gases as well.

Figure 4:
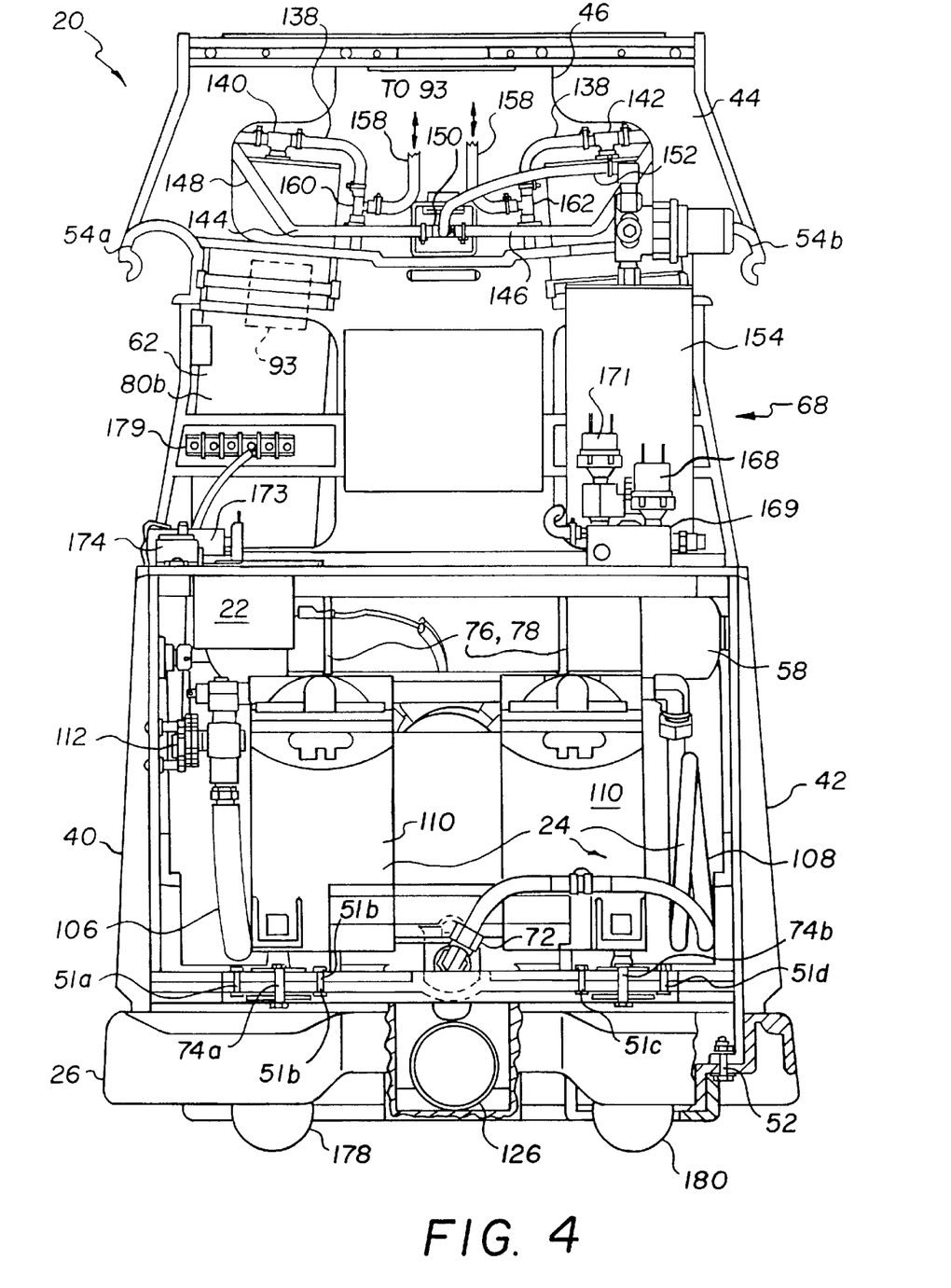
FIG. 4 is a view from the front of the FIG. 3 oxygen concentrator shown with its front cover removed.
Figure 5:
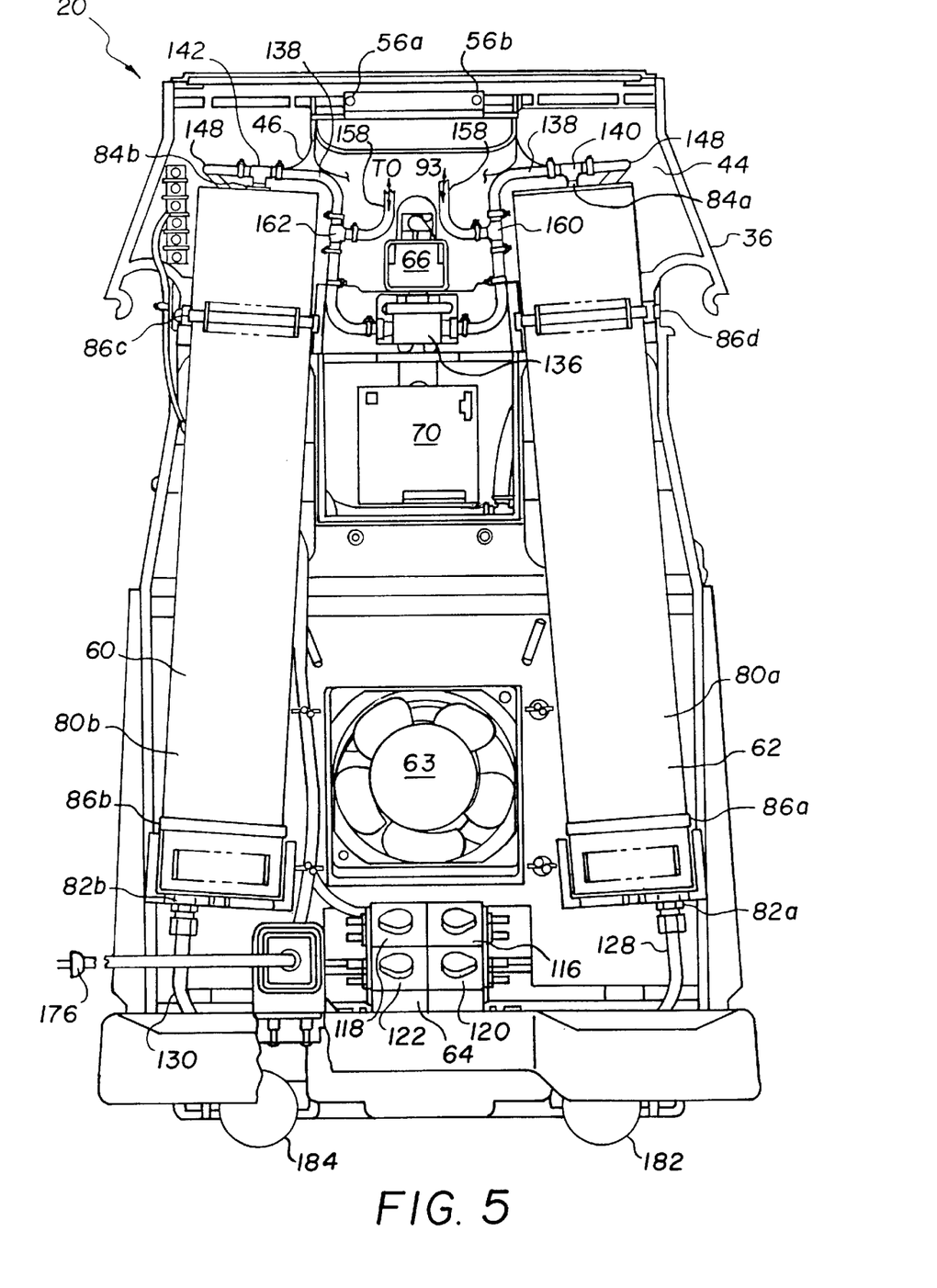
FIG. 5 is a view from the back of the FIG. 3 oxygen concentrator shown with its back cover removed.

The oxygen concentrator, 20 as shown in FIGS. 3, 4, and 5 includes a base 26 that supports housing 28, defining a cabinet assembly 34 with a removable back panel (not shown), a removable front panel 38, a removable left side panel 40, and a removable right side panel 42. The base 26 includes a fixed central support structure 44 that forms a back board for attaching components 30 through numerous apertures 46, as shown in FIGS. 4 and 5. Turning to FIG. 3, attached to the upper portion of structure 44 is a fixed upper front panel 48 that holds the control panel 50. Base 26, structure 44, panel 48, and cabinet assembly 34 are constructed of a suitably rigid material. The housing 28 provides a protective enclosure for the component assembly 30. Screws 51a, b, c, d, shown in FIG. 4, are utilized to join structure 44 to base 26. Screw 52 and latches 54a, b, 56a and b, as shown in FIGS. 4 and 5, are utilized to join the side panels 40, 42 to the base 26 and structure 44 and the front and back panels 36, 38 to the base 26 and side panels 40, 42 to thereby fixedly and releasably attach the panels 36, 38, 40, 42 to the base 26.

With further reference to FIG. 3 and 4, the working components 30 of the front side of the concentrator 20 include intake resonator 58, compressor assembly 24, control panel 50, pair of adsorbers 60, 62, and product flow control assembly 68. Turning to FIGS. 2 and 5, the working components 30 of the back side of the concentrator includes pair of adsorbers 60, 62, a fan 63, valve block 64, product manifold assembly 66, product flow control assembly 68 and a circuit board 70. The functions of these components 30 are described hereinafter.

Starting from the base 26 in FIGS. 4 and 5 and moving up the apparatus 20, the component assembly 30 attached to the base 26 comprises the compressor assembly 24 and the valve block 64. The compressor assembly 24, as shown in FIGS. 2 and 4, is conventional. It pumps air into the apparatus 20 and with the aid of fan 63 removes heat from the compressed air through heat exchanger 108. The assembly 24 is mounted to the base 26 by means of appropriate screws 74a, b.

The valve block 64, as shown in FIG. 5, includes a generally linear arrangement of items, hereinafter described, disposed immediately below and behind the compressor assembly 24, and oriented in a manner so as to extend generally at a 45 degree angle from the base 26. The valve block 64 is attached to the base 26 by means of a fastener, such as Velcro™.

Immediately above the base 26 are the intake resonator 58, the pair of adsorbers 60, 62 and the fan 63. The intake resonator 58, as shown in FIG. 4, is conventional and decreases the noise for the intake of air. It is mounted immediately above the fan 63. The intake resonator 58 is supportedly fastened to the central support structure 44 by means of tie wraps 76 and 78.

With particular reference to FIG. 5, each adsorber 60, 62 includes a substantially elongated vessel 80a, 80b supported to the structure 44 and having an interior cavity which is substantially filled with a bed of adsorption material adapted to adsorb nitrogen from air routed therethrough. Furthermore, each adsorber 62 or 60 includes an inlet 82a or 82b and an outlet 84a or 84b adjacent the lower and upper ends, respectively, of the corresponding adsorber vessel 80a or 80b wherein the inlet and outlet of each adsorber 60 or 62 are in flow communication with one another through the bed of adsorption material contained therein. Hence, air directed into each adsorber inlet 82a or 82b is exposed to the adsorption material, by which nitrogen in the air is adsorbed, and the resulting oxygen concentrated product gas then exits the corresponding adsorber through outlet 84a or 84b.

The adsorption beds of the adsorbers 60, 62 may be comprised of any of a number of adsorbent materials such as a molecular sieve material known as sodium alumina silicate. Characteristically, the adsorbent material adsorbs nitrogen from air routed through the corresponding adsorber 60 or 62 from the inlet 82b or 82a to the outlet 84b or 84a thereof so that the product oxygen gas exiting the adsorber outlet 84 is a desired concentration of oxygen gas. Furthermore, the adsorbent material releases its adsorbed nitrogen when a purge gas passes counter-currently through adsorber 62 or 60, for purposes of regenerating the adsorbent material. Only one of the adsorbers 60 or 62 performs adsorption at any one time while the other adsorber 60 or 62 undergoes regeneration. For increasing the efficiency of regeneration, an amount of product gas produced by the adsorber 60 or 62 performing adsorption is used to purge the other adsorber undergoing regeneration. Adsorbers 60, 62 are mounted to the central support structure 44 by means of tie wraps 86a, b, c, d.

Fan 63, shown in FIG. 5, is located immediately behind the compressor assembly 24. The fan 63 is a conventional fan that draws air into the apparatus 20 through a ventilation orifice (not shown) located on the back panel (not shown). The air circulates through the apparatus 20 to cool the components 30 and a portion of this air is drawn into intake 22 found in the intake resonator 58.

Immediately above the intake resonator 58 in the upper portion of apparatus 20 are the control panel 50 (FIG. 3), the circuit board 70 (FIG. 5), the product manifold assembly 66 and the product flow control assembly 68.

The control panel 50, as illustrated in FIG. 3, comprises panel instruments 90, such as a conventional flow controller valve 92 and a conventional concentration valve 93 [such as an Essex valve Model No. FM023-1 with variations in the orifice size], an hour-meter 94, a circuit breaker 96, an on/off switch 98, an outlet connector 100, and a supplemental oxygen connector 102. These panel instruments will be described hereinafter.

Many of these panel instruments 90 and working components 30 are electrically connected to circuit board 70. The circuit board 70, shown in FIGS. 5 and 8 and described hereinafter, is located immediately behind the ventilation orifice on the back panel and is mounted to the structure 44 by means of insulated standoffs.

The product manifold assembly 66, illustrated in FIG. 2, 4 and 5 includes items, hereinafter described, arranged in a generally linear arrangement and disposed immediately above the circuit board 70. These items include equalization valve 136, piping 138, 148, 158, purge orifices 144, 146, T-connections 140, 142, 150, 160, 162, and concentration valve 93.

The product flow control assembly 68 includes items, hereinafter described, disposed generally with the product manifold assembly 66. These items include piping 152, 167, 172, mixing tank 154, test block component 169, pressure regulator 170, flow controller valve 92, check valves 190a and 190b, and outlet connector 100.

As referenced above, the operation of the apparatus 20 initiates when the intake resonator 58 receives air through inlet 22. The resonator 58 is connected to the compressor assembly 24 by means of assembly piping 106.

As shown in FIG. 2 compressor assembly 24 includes conventional components such as a heat exchanger 108, compressor 110, a relief valve 112 and a high pressure switch 124. Valve 112 is operatively connected to compressor 110 through piping 106. In operation, valve 112 limits the pressure of the air supplied to the compressor 110 at a predetermined pressure. Similarly, high pressure switch 124 is operatively connected to heat exchanger 108 to limit the feed stream pressure to a predetermined limit. The high pressure switch 124 is a conventional switch that indicates high pressure within the valve block 64. The indicator can be either audio or visual or even both. The visual indicator is normally seen through conventional LED devices 132 found on the circuit board 70 (FIG. 8).

Figure 8:
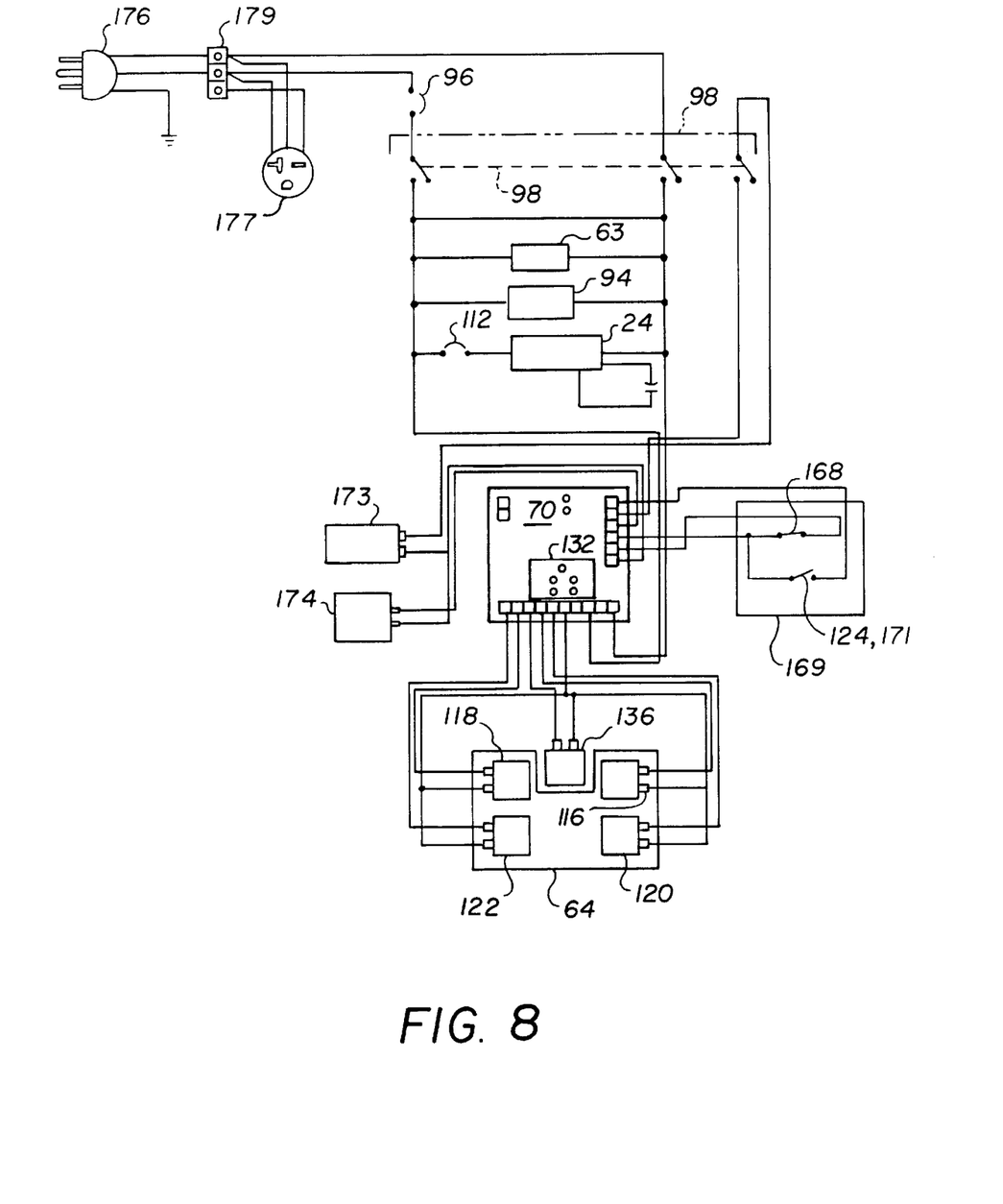
FIG. 8 is a schematic of the electrical system of the oxygen concentrator.

With reference to FIGS. 2 and 8, the valve block 64 is an integrated valving and porting system that ensures proper operation of various instruments. The instruments include a pair of feed valves 116, 118, a pair of waste valves 120, 122, and a waste silencer 126. The feed valves 116, 118 are connected between the heat exchanger 108 and the adsorber inlets 82a, 82b. In this connection, two sections of piping 128, 130 appropriately extend from the valve block 64 to the adsorber inlets 82a and 82b.

The waste valves 120 and 122 are interconnected with the adsorber inlets 82a, 82b and direct purge gas and the purged nitrogen in the counter-current direction through piping 128, 130 to silencer 126 and then to be discharged to the atmosphere through the silencer 126. Sounds normally associated with the discharging of a pressurized stream of gas to the atmosphere are muffled by the silencer 126.

As shown in FIG. 5, valves 116, 118, 120 and 122 are arranged in a generally square arrangement and as shown in FIG. 4, the silencer 126 is positioned below the valve block 64. Switch 124, as shown in FIG. 8, is connected to the circuit board 70.

Returning to FIG. 2, the product manifold assembly 66 is receives the product gas from the outlets 84b, 84a of the adsorbers 60 and 62 and includes a product and equalization valve 136 for equalizing the internal pressure of the adsorbers 60 and 62 between product-producing and regeneration cycles. The product equalization valve 136 is operatively connected to the adsorber outlets 84a and 84b by means of piping 138 and T-connections 140 and 142. By opening the valve 136, the adsorber vessels 80a, 80b communicate with one another through the adsorber outlets 84a, 84b in a manner permitting the internal pressure of the adsorbers 60 and 62 to equalize. By closing the valve 136, flow of gaseous product between the adsorber outlets 84a and 84b through the valve 136 is prevented.

Furthermore, and with reference to FIG. 2, a pair of purge orifices 144, 146 are connected in parallel flow relation to the product equalization valve 136 by way of piping section 148 between T-connections 140 and 142 and a third T-connection 150. In operation, the orifices 144, 146 limit the purge flow of product oxygen gas that goes through adsorbers 60, 62 counter-currently to obtain the optimal high concentration product oxygen gas. The orifices 144, 146 also dampen, only in correlation with concentration valve 93, the product oxygen gas pressure excursions, as illustrated in FIG. 7, that proceed through T-connection 150 to piping 152 which is connected to a mixing tank 154.

Along with equalizing the internal pressure of the adsorbers 60 and 62, there is illustrated according to the invention a second purge loop 156 including a section of purging piping 158 that is connected in parallel flow relation to the product equalization valve 136 and pure orifices 144, 146 by means of T-connections 160, 162 on piping 138. Interconnected to the purge piping 158 is the concentration valve 93. Valve 93 comprises multiple orifices ranging from a minimal flow rate to a maximum flow rate which can be altered to attain different desired concentrations of product gas. In table 1, below, symbols A–G represent the various orifice sizes that provide different quantities of product gas within the purge loop 156 with A being the minimum and G being the maximum.

During a regeneration operation of one of the adsorbers 60, 62, concentration valve 93 is manually, or if so desired automatically, set to allow a certain quantity of product oxygen gas to move between the outlets 84a, 84b of the adsorbers 62, 60. As the quantity of product oxygen gas flowing through the concentration valve 93 increases the MTZ 10 of the adsorber spreads through the bed of adsorbent 2, as illustrated in FIG. 6 up to line 10c, in a controllable manner while simultaneously stabilizing the water zone 6. In other words, if the quantity of product gas flowing through valve 93 is decreased, the MTZ 10 of the adsorber becomes sharper (as shown in line 10a) similar but not equal to the 95% oxygen stream illustrated in FIG. 1A. Thereby, the MTZ 10 of the adsorber 60 is controllable, as shown by arrows 164, to produce a resulting product oxygen gas of desired concentration from a range of available concentrations. The resulting product oxygen gas has a manageable and controllable concentration range by reducing the pressure excursions of the gas, as illustrated in FIG. 7, that can be further controlled through the product flow control assembly 68 described hereinafter.

When the product oxygen gas exits the product manifold assembly 66 as shown in FIG. 2, the product gas enters the flow control assembly 68 through mixing tank 154 to average the concentration of the product gas. The tank 154 is mounted to structure 44. Moreover, mixing tank 154 can even contain an adsorbent material, for example those used in adsorber 60, 62 to ensure the nitrogen is averaged in the product gas.

Figure 9:
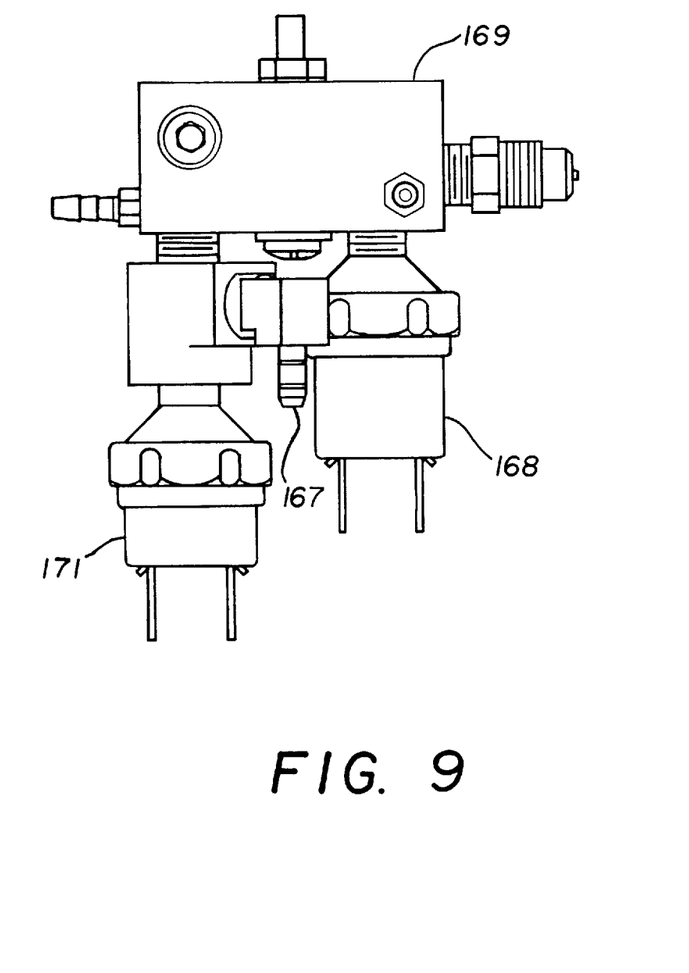
FIG. 9 is a view of a test block valve according to the present invention.

The remainder of the product flow control assembly 68 is connected to the mixing tank 154 through piping 167 for receiving the product oxygen gas flowing therethrough. The product flow control assembly 68 comprises the flow controller valve 92, pressure regulator 170 that maintains a desired concentration range, and test block component 169 as shown in FIG. 9. The test block component 169 includes a low pressure switch 168 and a high pressure switch 171 for sensing pressure of the product oxygen gas at preselected locations in piping 167. Switches 168 and 171 are interconnected with control panel 50.

Valves 92 and 93 each comprise many various orifices. These orifices can be manually set (or automatically if so desired) to control the flow of the product oxygen gas or to achieve the desired concentration of product oxygen gas ranging in relation with the concentration valve 93 from about ninety-five point five (95.5) percent oxygen to about twenty-one (21) percent oxygen with the preferable ranges as illustrated in Table 1.

TABLE 1

| Concentration Valve | Percent O$_2$ Concentration (Flow Controller Valve) Liters per Minute | | | | | | | | | |
|---|---|---|---|---|---|---|---|---|---|---|
| Position | 06 | 07 | 08 | 09 | 10 | 11 | 12 | 13 | 14 | 15 |
| A | 77 | 72 | 67 | 62 | 56 | 53 | 50 | 48 | 46 | 45 |
| B | 57 | 55 | 54 | 53 | 51 | 50 | 48 | 47 | 45 | 44 |
| C | 51 | 50 | 49 | 47 | 47 | 46 | 45 | 44 | 44 | 43 |
| D | 46 | 45 | 45 | 44 | 44 | 43 | 42 | 42 | 42 | 41 |
| E | 43 | 43 | 42 | 42 | 42 | 41 | 40 | 40 | 39 | 39 |
| F | 41 | 41 | 41 | 40 | 40 | 39 | 39 | 39 | 39 | 39 |
| G | 40 | 40 | 39 | 39 | 39 | 38 | 38 | 37 | 37 | 37 |

Attached to the discharge or downstream side of the flow controller valve 92 is a section of piping 172 which is connected to outlet connector 100 on panel 50 through which product oxygen gas exits the concentrator 20.

Operation of the oxygen concentrator 20 can be described briefly through a description of the sequencing of the valving means of the concentrator 20 as illustrated in FIGS.

2 and 8. At start-up of the concentrator 20, valves 116, 118, 120, 122, and 136 are open to eliminate the back pressure and then closed through a timing mechanism of conventional switches and relay switches printed on the circuit board 70. The source air entering the concentrator 20 through inlet 22 is thereby directed through the adsorber 62 from its inlet 82a to its outlet 84a in a co-current direction. An amount, dependent upon the orifice size of the concentrator valve 93 selected, of oxygen emitted from the adsorber outlet 84a is directed in parallel through valve 93 and in part through orifices 144, 146 in a counter current direction, through adsorber 60 from outlet 84b to inlet 82b thereof, and through waste valve 122 which opens by the timing mechanism. The balance of the resulting product gas of the desired oxygen concentration is delivered to the mixing tank 154.

The operation continues until the adsorber 62 becomes about saturated. The determination of when the adsorber is about saturated has been predetermined and is controlled through the timing mechanism which controls the various valves 116, 118, 120 122 and 136. When this occurs to the adsorber 62 the feed valve 116 and the waste valve 122 are closed and the equalization valve 136 is opened to permit the internal pressures of adsorbers 60, 62 to equalize. Once the adsorber pressures are equalized, the equalization valve 136 is closed and the feed valve 118 for adsorber 60 and waste valve 120 for adsorber 62 are opened. The source air entering the concentrator 20 through the inlet 22 is thereby directed through the adsorber 60 from its inlet 82b to its outlet 84b in a co-current direction. Similarly, an amount, dependent upon the orifice size of the concentrator valve 93 selected, of oxygen emitted from the adsorber outlet 84b is directed through valve 93 and orifices 144, 146 in a counter current direction, through adsorber 62 from outlet 84a to inlet 82a thereof, and through waste valve 120. The resulting product oxygen gas has a desired concentration in accordance with the setting of valve 93.

When the adsorber 60 becomes about saturated and purged the feed valve 118 and waste valve 120 are closed and the equalization valve 136 is opened to thereby permit the internal pressures of the adsorbers 60, 62 to equalize. At that point, the cycles of operation are repeated with the closing of equalization valve 136 and reopening of feed valve 116 and waste valve 122. It follows that while one adsorber produces oxygen-rich product gas in a product-producing cycle, the other adsorber is being purged of the adsorbed gases in a regeneration operation, and vice-versa.

Each of the aforementioned feed, waste, and equalization valves is preferably a solenoid-type valve responsive to a turning on or shutting off of power to the valve. Control of the various product-producing and regeneration operations is conducted by appropriately sequencing the opening and closing of the aforedescribed feed, waste, and equalization valves. In the concentrator 20, control of the aforedescribed valves is achieved by timing mechanisms of conventional switches and relays printed on circuit board 70. The timing mechanism is operatively connected to the valves for turning the valves ON and OFF at the end of a predetermined period of time. Hence, product-producing and regeneration operations are automatically controlled in the concentrator 20 by automatically controlling the amount of time that each of the feed, waste, and equalization valves are opened and closed.

The timing mechanism printed on the circuit board 70 controls these numerous valves through conventional circuitry, and switches known to skilled practitioners, as illustrated in FIG. 8. The board 70 is also connected to a battery unit 173, and buzzer 174, and comprises LED devices 132. The buzzer 174 is connected to switches 124, 168, 171. Power is generally received through an electrical connection, such as an electrical plug 176 and a secondary external power source 177. Plug 176 and source 177 are interconnected by connector 179 as shown in FIGS. 3 and 8. The power is supplied through a circuit breaker 96 and master power switch 98 to the circuit board 70. The circuit board 70 then directs and controls the valves 116, 118, 120, 122, and 136, panel instruments 90, compressor assembly 24 with a high temperature cut off switch 112 in series, and fan 63. In case of an emergency, the apparatus 20 has the battery unit 173 that is electrically connected to the circuit board 70. When the battery unit 173 is operating, the buzzer 174 warns the user.

In other embodiments of the present invention, the electrical circuitry can be connected to a conventional modem system (not shown) which determines the operation times and settings and allows an administrator to control the settings of the valves 116, 118, 120, 122 and optionally, the settings of valves 92 and 93 if these valves are connected to circuit board 70.

The housing means 28 can be made of conventional soundproof materials, and the base 26 can have wheels 178, 180, 182, 184 as shown in FIGS. 3 and 4.

It will be understood that numerous modifications and substitutions will be had to the aforedescribed embodiment without departing from the spirit of the invention. Accordingly, the aforedescribed embodiment is intended for purposes of illustration and not as a limitation.

I claim:

1. In a pressure swing adsorption apparatus having at least two multi-zone adsorbers, each adsorber having a mass transfer zone to adsorb a portion of at least one constituent gas in a gaseous mixture of at least two gaseous constituents, a method for selectively changing the relative concentrations of the other constituent gas to produce a product gas with a desired concentration of the other constituent gas and selected from one of a number of different concentrations of the other constituent gas in the product gas, said method comprising:

alternately moving, at a predetermined flow rate, the gaseous mixture in a co-current direction through each one of the adsorbers to produce the product gas and for moving the product gas in an opposite, counter-current direction through the other adsorber to purge said second adsorber by adsorbing at least a substantial portion of the one constituent gas;

moving a predetermined portion of the product gas produced by each one of the adsorbers in the counter-current direction through the other adsorber to sufficiently purge the adsorbed one constituent gas from the other adsorber;

diverting from said one adsorber a variable portion of the product gas, in addition to the predetermined portion, to said other adsorber in the counter-current direction to control, independently of the flow rate, the location of the mass transfer zone and the amount of adsorption of the one constituent gas in said one adsorber to produce the product gas with the desired concentration of the other constituent gas; and delivering to a receiving means the balance of the product gas having the desired concentration of the other constituent gas.

2. The method as claimed in claim 1 further comprising the step of a product gas that has a desired concentration and flow rate, wherein the flow rate and controlling, independently of the step of diverting the variable portion of the product gas, the flow rate of the delivered product gas within a predetermined range of flow rates.

3. The method as claimed in claim 2 wherein the step of controlling the mass transfer zones comprises the step of passing the diverted product gas through an orifice and selecting the orifice size to divert the desired amount of product gas.

4. The method as claimed in claim 2 wherein the predetermined range of flow rates is from about 6 to about 15 liters per minute.

5. The method as claimed in claim 1 wherein the step of controlling each of said mass transfer zones comprises the step of passing the diverted product gas through an orifice and selecting the orifice size to divert the desired amount of product gas.

6. The method as claimed in claim 5, in which each adsorber includes a zone to substantially adsorb any water in the gaseous mixture, and further comprising the step of controlling and stabilizing the water adsorption zone of said adsorber.

7. The method as claimed in claim 1 wherein the step of diverting the variable portion of product gas produces, in a range from about ninety-five point five to about twenty-one percent, the concentration of the other constituent gas in the usable product gas.

8. The method as claimed in claim 7 wherein the range of concentration of the other constituent gas in the product gas is from about seventy-seven to about thirty-seven percent.

9. A pressure swing adsorption apparatus for selectively changing the relative concentrations of constituent gases in a gaseous mixture of two or more constituent gases, comprising:

first and second adsorbers, each adsorber defining an inlet and an outlet for inflow and outflow of the constituent gases into and from the adsorber, each adsorber further defining a plurality of gas transfer zones disposed between the inlet and outlet one of the zones comprising a mass transfer zone wherein at least a substantial portion of one of the constituent gases in the gaseous mixture is adsorbed by the adsorber, the remainder of the gaseous mixture comprising a product gas of increased concentration of the other of said constituent gases;

means for selectively causing the gaseous mixture and the product gas to flow through each adsorber in a co-current direction from the inlet and toward the outlet of the adsorber and to flow in a counter-current direction from the outlet toward the inlet of the adsorber;

valve means fluidly connected to the flow causing means and the adsorbers for selectively directing the flow of the gaseous mixture alternately through each one of the adsorbers in the co-current direction to produce the product gas;

a receiving tank fluidly coupled to the outlets of the adsorbers and means for delivering to the receiving tank at least a portion of the product gas flowing from the adsorbers in the co-current direction;

purge means fluidly connected to the output of each of the adsorbers for directing a predetermined portion of the product gas produced by the one adsorber to flow through the other adsorber in the counter-current direction to sufficiently purge and expel from the other adsorber, through the other adsorber's inlet the one constituent gas adsorbed by the other adsorber; and adjustable zone controlling means fluidly connected to the adsorbers for selectively changing the concentration of the constituent gases in the product gas delivered to the receiving tank by selectively diverting from the one adsorber variable portions of the product gas, in addition to the predetermined portion of product gas, to the outlet of the other adsorber for controlling the location of at least the mass transfer zone in the one adsorber to produce a desired one from a number of selectable concentrations of the other constituent gas in the product gas delivered to the receiving tank.

10. The pressure swing adsorption apparatus of claim 9 further comprising means for selectively controlling the flow rate of the product gas to increase the available number of selectable concentrations of the other constituent gas in the product gas delivered to the receiving tank.

11. The pressure swing adsorption apparatus of claim 10 wherein the adjustable zone controlling means comprises a valve defining an orifice and means for selecting the orifice size from a variation of orifice sizes.

12. The pressure swing adsorption apparatus of claim 10 wherein said means for selectively controlling the flow rate produces a desired flow rate of product gas ranging from about 6 to about 15 liters per minute.

13. The pressure swing adsorption apparatus of claim 9 wherein said receiving tank comprises a mixing tank containing an adsorbent material to average the concentration of the other constituent gas in the product gas received by the mixing tank.

14. The pressure swing adsorption apparatus of claim 9 wherein said adjustable zone controlling means comprises a valve defining an orifice in the fluid connection to the adsorbers and of a size to divert the portion of additional product gas and means for selecting the orifice size from a variation of orifice sizes.

15. The pressure swing adsorption apparatus of claim 9 further comprising means for automatically controlling the operation of said adjustable zone controlling means.

16. The pressure swing adsorption apparatus of claim 9 wherein said adjustable zone controlling means selectively changes in a range from about ninety-five point five to about twenty-one percent, the concentration of the other constituent gas in the product gas delivered to the receiving tank.

17. The pressure swing apparatus of claim 16 wherein the range of concentration of the other constituent gas in the delivered product gas is from about seventy-seven to about thirty-seven percent.

18. The pressure swing adsorption apparatus of claim 9 wherein said gaseous mixture is air.

19. The pressure swing adsorption apparatus of claim 9 wherein the other constituent gas in said product gas is oxygen.

20. The pressure swing adsorption apparatus of claim 9 wherein each adsorber further defines a water adsorption zone in which any water in the gaseous mixture is substantially adsorbed, and said adjustable zone controlling means further stabilizes the water adsorption zone.

21. In a pressure swing adsorption apparatus for selectively changing the relative concentrations of constituent gases in a gaseous mixture of two or more constituent gases, comprising:

(a) at least two adsorbers, each adsorber having two ends and comprising (i) means for receiving the gaseous mixture at one end of the adsorber, (ii) means for moving the gaseous mixture through the adsorber in a co-current direction, (iii) means defining a plurality of gas transfer zones including a mass transfer zone for adsorbing at least a substantial portion of one of the constituent gases in the gaseous mixture to produce a product gas, and (iv) means for discharging the product gas from the other end of the adsorber;

(b) means for directing the gaseous mixture in the co-current direction alternately to each of the adsorber receiving means;

(c) means fluidly coupled to both discharging means for receiving as output a portion of the product gas discharged in the co-current direction from each of the other ends of the adsorbers; and (d) purge means fluidly connecting the other ends of both adsorbers for directing a predetermined portion of the product gas flowing in the co-current direction from one adsorber to flow through the other adsorber, in a counter-current direction, from the other end to the one end of the other adsorber, to purge and expel through the one end of the other adsorber, a sufficient amount of the one constituent gas adsorbed by the other adsorber; the improvement comprising (e) adjustable zone controlling means fluidly connected to the adsorbers for selectively changing the concentrations of the constituent gases in the portion of product gas delivered to the receiving means by selectively diverting, in addition to the predetermined portion, variable amounts of product gas discharged from the one adsorber to flow through the other adsorber in the counter-current direction to control the location of at least the mass transfer zone in the one adsorber and produce a selected one of a number of concentrations of the other constituent gas in the product gas received by the receiving means.

22. The pressure swing adsorption apparatus of claim 21 wherein the adjustable zone controlling means comprises valve means defining an orifice of a size to divert the selected amount of additional product gas, and means for selecting the orifice size from a variation of orifice sizes.

23. The pressure swing adsorption apparatus of claim 21 and further comprising means for controlling the rate of flow of the product gas.

24. The pressure swing adsorption apparatus of claim 23 wherein the adjustable zone controlling means comprises valve means defining an orifice of a size to divert the selected amount of additional product gas, and means for selecting the orifice from a variation of orifice sizes.

25. The pressure swing adsorption apparatus of claim 23 wherein the adjustable zone controlling means and the flow rate controlling means selectively change, in a range from about ninety-five point five to about twenty-one percent, the concentration of the other constituent gas in the portion of product gas received by the receiving means.

26. The pressure swing apparatus of claim 25 wherein the range of concentration is from about seventy-seven to about thirty-seven percent.

27. The pressure swing adsorption apparatus of claim 23 wherein the flow rate controlling means produces a selected flow rate of the product gas in a range from about 6 to about 15 liters per minute.

28. The pressure swing adsorption apparatus of claim 21 wherein one of the gas transfer zones of each adsorber comprises a water adsorption zone to substantially adsorb any water in the gaseous mixture, and the adjustable zone controlling means further stabilizes the water adsorption zone.

29. The pressure swing adsorption apparatus of claim 21 wherein the one constituent gas comprises nitrogen and the other constituent gas comprises oxygen.

* * * * *

UNITED STATES PATENT AND TRADEMARK OFFICE
CERTIFICATE OF CORRECTION

PATENT NO. : 5,871,564
DATED : February 16, 1999
INVENTOR(S) : Norman Richard McCombs It is certified that error appears in the above-identified patent and that said Letters Patent is hereby corrected as shown below:

On the title page, add --[73] Assignee: AirSep Corporation, Buffalo, N.Y. --.

Column 4, line 39, change "reduced" to --replaced--.

Column 10, lines 65-66 delete "a product gas that has a derived concentration and flow rate, wherein the flow rate and".

Signed and Sealed this

Twelfth Day of October, 1999

Attest:

Q. TODD DICKINSON

*Attesting Officer*     *Acting Commissioner of Patents and Trademarks*